United States Patent [19]

Peglion et al.

[11] Patent Number: 5,298,503

[45] Date of Patent: Mar. 29, 1994

[54] N-(ISOQUINOLIN-5-YLSULPHONYL) AZACYCLOALKANES

[75] Inventors: Jean-Louis Peglion, Le Vesinet; Jean-Paul Vilaine, Chatenay Malabry; Nicole Villeneuve, Rueil Malmaison; Philip Janiak, Clichy, all of France

[73] Assignee: Adir et Compagnie, Courbevoie, France

[21] Appl. No.: 922,992

[22] Filed: Jul. 30, 1992

[30] Foreign Application Priority Data

Jul. 31, 1991 [FR] France ................................ 91 09720

[51] Int. Cl.$^5$ ..................... C07D 401/12; A61K 31/47
[52] U.S. Cl. ..................... 514/212; 514/307; 514/309; 540/597; 546/139; 546/141; 546/146; 546/147; 546/148
[58] Field of Search ............... 546/141, 146, 147, 148, 546/139; 514/212, 309, 307; 540/597

[56] References Cited

FOREIGN PATENT DOCUMENTS 62-111981 5/1987 Japan .

OTHER PUBLICATIONS

Chemical Abstracts Service: CA108(5):37665v, 1987.

*Primary Examiner*—Marianne M. Cintins
*Assistant Examiner*—Catherine Scalzo
*Attorney, Agent, or Firm*—Gordon W. Hueschen

[57] ABSTRACT

Compounds of formula (I):

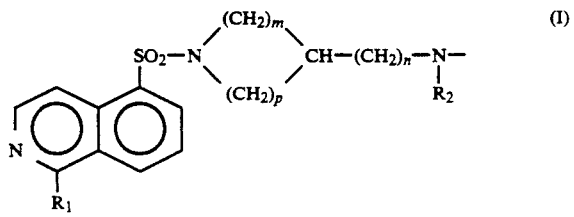

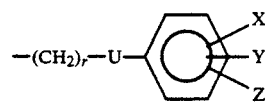

wherein $R_1$, $R_2$, U, X, Y, Z, n, m, p and r are as defined in the description, and medicaments containing the same.

8 Claims, No Drawings

N-(ISOQUINOLIN-5-YLSULPHONYL) AZACYCLOALKANES

The present invention relates to new N-(isoquinolin-5-ylsulphonyl)azacycloalkanes, to a process for the preparation thereof, and to pharmaceutical compositions containing them.

It relates more especially to the compounds of formula (I):

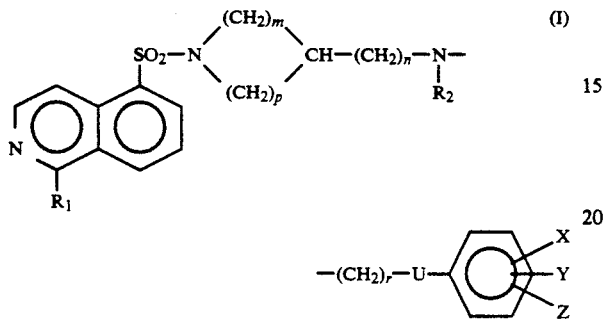

in which:

n is 0 or an integer from 1 to 3,
m and p are integers from 1 to 4 with the proviso that the sum of m+p is 2, 3, 4 or 5,
r is an integer from 1 to 6,
$R_1$ represents a hydrogen atom, a hydroxy group or a chlorine atom,
$R_2$ represents:
  a hydrogen atom,
  a formyl group,
  a group —A, —CO—A or —CO—O—A, wherein A represents a lower alkyl, lower alkenyl, lower alkynyl, cycloalkyl or cycloalkyl-lower alkyl group,
  a —$(CH_2)_q$-phenyl group or a substituted —$(CH_2)_q$-phenyl group, wherein q represents 0 or an integer from 1 to 4,
  a —CO-phenyl group or a substituted —CO-phenyl group,
  a —CO—O-phenyl group or a substituted —CO—O-phenyl group, or
  a group —CO—$NR_4R_5$, wherein $R_4$ and $R_5$ which may be identical or different, each represent a hydrogen atom or a group selected from lower alkyl, lower alkenyl, lower alkynyl, phenyl and phenyl-lower alkyl, or
  together with the nitrogen atom carrying them, form a saturated ring having from 4 to 7 ring members,
X, Y and Z, which may be identical or different, each independently of the others represent a hydrogen atom, a halogen atom, or a group selected from lower alkyl, lower alkoxy, nitro, amino, cyano, acetamido and carboxamido, or X and Y, or X and Z, together form, with the two carbon atoms of the phenyl nucleus carrying them, a furan, dihydrofuran or benzene ring,
U represents an oxygen atom, a sulphur atom or a group selected from: carbonyl, sulphinyl, sulphonyl, —NH—CO—, —CO—NH—, —O—$(CH_2)_{r'}$—O— wherein r' represents an integer 2 Or 3, —$(CH_2)_{r''}$—O—$(CH_2)_{r'''}$— wherein r'' and r''' each represent integers 1 or 2, and —N—
    |
    $R_3$ wherein $R_3$ represents :
  a hydrogen atom,
  a formyl group,
  a group —A, —CO—A or —CO—O—A, wherein A represents a lower alkyl, lower alkenyl, lower alkynyl, cycloalkyl or cycloalkyl-lower alkyl group,
  a —$(CH_2)_q$-phenyl group or a substituted —$(CH_2)_q$-phenyl group, wherein q represents 0 or an integer from 1 to 4,
  a —CO-phenyl group or a substituted —CO-phenyl group,
  a —CO—O-phenyl group or a substituted —CO—O-phenyl group, or
  a group —CO—$NR_4R_5$, wherein $R_4$ and $R_5$ are as defined above,
  wherein the term "substituted" relating to the groups —$(CH_2)_q$-phenyl, —CO-phenyl or —CO—O-phenyl means that those groups may be substituted by one or more radicals selected from: lower alkyl, lower alkoxy, hydroxy, halogen and trifluoromethyl,
and wherein the terms "lower alkyl" and "lower alkoxy" indicate straight-chained or branched saturated carbon-containing groups containing from 1 to 6 carbon atoms,
  the terms "lower alkenyl" and "lower alkynyl" designate straight-chained or branched unsaturated groups containing from 2 to 6 carbon atoms, and
  the term "cycloalkyl" designates a saturated carbon-containing ring containing from 3 to 8 ring members.

There are known from the literature compounds having an isoquinolinesulphonamide structure which exhibit in particular anti-aggregation activity (JP 63-325910), vasodilatory activity (EP 109023) or bronchorelaxant activity (U.S. Pat. No. 4857301).

The prior art also includes the following documents: JP 02073067, EP 187371 and EP 061673.

Important structural modifications have led to the compounds of the present invention, which have a particularly powerful and extensive anti-vasoconstrictive pharmacological activity, which is not found in the compounds of the prior art.

The present invention relates also to the process for the preparation of the compounds of formula (I), characterised in that:

a compound of formula (II):

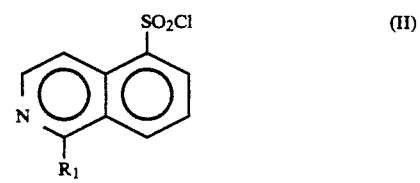

in which $R_1$ has the same meaning as in formula (I), is reacted
either with a compound of formula (III):

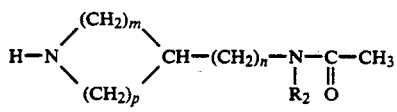

in which $R_2$, n, m and p have the same meaning as in formula (I),
to obtain, after acid hydrolysis, a compound of formula (IV):

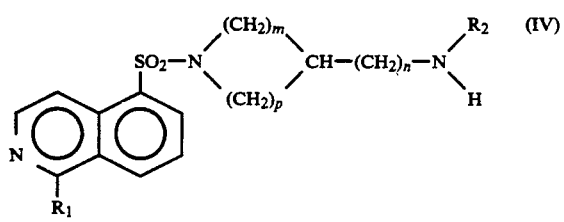

in which $R_1$, $R_2$, n, m and p are as defined above, which is reacted with a compound of formula (V):

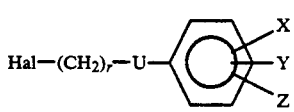

in which X, Y, Z, U and r have the same meaning as in the general formula (I) and Hal represents a halogen atom, to obtain a compound of formula (I):

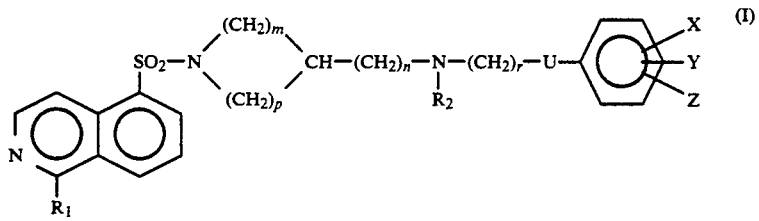

in which $R_1$, $R_2$, U, X, Y, Z, n, m, p and r are as defined in formula (I),
or with a compound of formula (VI):

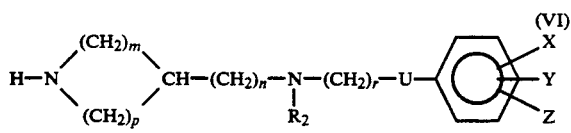

in which $R_2$, U, X, Y, Z, n, m, p and r are as defined above, to obtain a compound of formula (I), the isomers of which, where applicable, are separated, and which, if desired, is converted into a salt with a pharmaceutically acceptable acid, which compound of formula (I) is purified, if desired, by a method of crystallisation and/or chromatography.

The starting materials used in the processes described above are either known products or products prepared from known substances, according to processes described for preparing analogous products as indicated in the Examples below.

The compounds of formula (I) can be converted into addition salts with acids, which salts, as such, form part of the invention. As acids which may be used for the formation of those salts there may be mentioned, for example, from the mineral series, hydrochloric acid, hydrobromic acid, sulphuric acid and phosphoric acid, and, from the organic series, acetic acid, propionic acid, maleic acid, fumaric acid, tartaric acid, nitric acid, oxalic acid, benzoic acid, methanesulphonic acid, isethionic acid, benzenesulphonic acid, etc..

Moreover, where there exist one or more asymmetric carbons, the compounds of formula (I) may be in the form of diastereoisomers or enantiomers which, as such, in pure form or in the form of a mixture, are part of the invention.

The compounds of formula (I) and their pharmaceutically acceptable addition salts have valuable therapeutic properties, especially in the cardiovascular field.

Pharmacological tests carried out in vitro have shown that those products have a powerful anti-vasoconstrictive activity with regard to the various types of processes involved in the contraction of smooth muscle, and especially with regard to intracellular processes involving intracellular calcium.

Those properties therefore allow the compounds of the present invention to be used as medicaments, especially in the cardiovascular field in the treatment and prevention of myocardial ischaemia and its various clinical manifestations such as angina pectoris and myocardial infarction, but also in the prevention and treatment of disturbances in cardiac rhythm, of vascular spasm, of arterial hypertension, of vascular disorders and of cardiac insufficiency, and more generally in the treatment and prevention of disorders associated with arterial ageing and with atherosclerosis.

Those compounds may also be administered for the prevention of vascular re-stenoses or thromboses following bypass surgery, vascular, especially coronary, dilatation, or other forms of vascular repermeabilisation. They may also be used in metabolic pathologies which constitute a cardiovascular risk factor, such as obesity, diabetes and dyslipidaemias.

Furthermore, as a result of the regulatory effect of those products on intracellular calcium, it is possible to use them therapeutically as platelet anti-aggregation and anti-thrombotic agents or as relaxant agents for various types of smooth muscles (other than the vascular muscles already mentioned): bronchial, digestive, urinary or uterine.

Moreover, many conditions of tissue damage, whether they be associated with ageing, with ischaemia, with inflammation or with cell proliferation, can be treated or prevented by means of the products of the present invention.

The pharmaceutical compositions so obtained are generally in dosage unit form. They may be in the form of, for example, tablets, dragées, gelatin capsules, suppositories, or injectable or drinkable solutions, and may be administered by the oral, rectal, intramuscular or parenteral route.

The dosage may vary considerably according to the age and weight of the patient, the mode of administration, and the nature of the disorder and associated treatments, and consists of doses of from 1 to 100 mg, one to several times per day.

The following Examples illustrate the invention but do not limit it in any way.

Melting points are determined using a Köfler hot plate. 1H Nuclear magnetic resonance spectra (NMR) were carried out using tetramethylsilane (TMS) as internal reference. Chemical shifts are expressed in parts per million (ppm). Infra-red spectra were effected in the form of a potassium bromide pellet containing approximately 1% of the product to be analysed.

EXAMPLE 1

Fumarate of 1-(isoquinolin-5-ylsulphonyl)-4-{N-methyl-N-[4-(p-fluorophenoxy)butyl]amino}piperidine

Step A 1-benzyl-4-(methylamino)piperidine

A solution of 1 mol of N-benzylpiperid-4-one in 2200 cm$^3$ of isopropanol is cooled to 18° C. A freshly prepared solution of 3 mol of methylamine in 300 cm$^3$ of methanol is added to the first solution. The mixture is left at that temperature for one hour.

1.66 mol of sodium hydroxide in the form of pellets are added. 1.37 mol of sodium borohydride are added at a constant temperature of 18° C. The mixture is allowed to return to room temperature and then the reagents are left in contact for 12 hours. The solvents are evaporated, and the residue is taken up in ether and then washed with water. Drying and evaporation yield an oil which is the desired compound. Yield: 78%.

Step B 1-benzyl-4-(N-methyl-N-acetylamino)piperidine

A solution consisting of 132 g (0.647 mol) of the compound obtained in the preceding step and 65.4 g of triethylamine in 1300 cm$^3$ of methylene chloride is prepared. 45.9 cm$^3$ of acetyl chloride are added slowly. The reagents are left in contact for 2 hours. Evaporation is carried out, and the residue is taken up in ether and then washed with water. Drying and evaporation of the solvent yield 128 g of an oil which corresponds to the desired compound and which will be used without further purification.

Step C 4-(N-methyl-N-acetylamino)piperidine 0.38 mol of the compound obtained in the preceding step is hydrogenated in 700 cm$^3$ of ethanol and 0.38 mol of acetic acid under a pressure of 5 kg/cm$^2$ in the presence of 9 g of palladium hydroxide.

After filtration and evaporation, the residue is taken up in 500 cm$^3$ of methylene chloride, and the mixture is rendered basic, while cold, with 0.38 mol of 20% sodium hydroxide, with stirring. The mixture is decanted, dried and then evaporated, yielding 49.7 g of the desired compound.

Yield: 83%.

Melting point: <50° C.

Step D 1 (isoquinolin-5-ylsulphonyl)-4-(N-methyl-N-acetylamino) piperidine

A solution of 13.7 g (0.0879 mol) of the compound obtained in the preceding step and 22.5 g of diisopropylethylamine in 950 cm$^3$ of methylene chloride is prepared. 23.3 g (0.0879 mol) of the finely powdered hydrochloride of 5-isoquinoline sulphochloride are added, with stirring and at room temperature. The mixture is decanted into a separating funnel and washed with 90 cm$^3$ of sodium hydroxide and then with water. The mixture is dried and evaporated. The resulting oil is chromatographed over silica using as elution system a methylene chloride/methanol mixture (95/5), yielding 17 g of a solid which corresponds to the desired compound.

Yield: 58%.

Melting point: 194°–196° C.

Step E 1-(isoquinolin-5-ylsulphonyl)-4-(methylamino)piperidine

A mixture comprising 0.051 mol of the compound obtained in the preceding step, 160 cm$^3$ of concentrated hydrochloric acid and 160 cm$^3$ of water is refluxed for a period of 12 hours. The mixture is cooled, rendered basic with 20% sodium hydroxide, and then extracted with ethyl acetate. The oil obtained after evaporation is subjected to chromatography over silica using as elution system a methylene chloride/methanol mixture (80/20), yielding 4.5 g of the desired compound.

Step F 1 bromo-4-(p-fluorophenoxy)butane 0.5 mol of potassium hydroxide is dissolved in 200 cm$^3$ of methanol. 0 5 mol of p-fluorophenol, 3.4 mol of 1,4-dibromobutane and 3 mmol of potassium iodide are added. The mixture is refluxed, with stirring, for 24 hours.

After evaporation of the solvent, the residue is taken up in ether and washed with water and then with 1N sodium hydroxide. After removal of the excess dibrominated compound, the residue is distilled using a Kughelrohr system.

An oil which is the desired compound is obtained.

Yield: 66%.

B.p.(1.33 Pa) =100° C.

Step G 1-(isoquinolin-5-ylsulphonyl)-4-{N-methyl-N-[4-(p-fluorophenoxy)butyl]amino}piperidine A solution consisting of 5.4 g of the compound obtained in step E, 0.0177 mol of the compound obtained in step F, 2.5 g of potassium carbonate and 50 cm$^3$ of acetone is prepared.

The mixture is refluxed, with stirring, for 12 hours. After evaporation, the residue is taken up in ether, and then the ethereal phase is exhaustively extracted with 1N hydrochloric acid. The acidic phases are rendered basic while cold, extracted with ether and dried. Evaporation yields 8.4 g of an oil, which is chromatographed over silica using as elution system a toluene/methanol mixture (95/5).

There are obtained 3 g of oil which corresponds to the desired compound.

Step H

Title compound

The 3 g of compound obtained in the preceding step are taken up in 18.5 cm$^3$ of a 0.172 molar solution of fumaric acid in ethanol. The resulting solution is evaporated to dryness and then the residue is taken up, with stirring for 12 hours, in 10 cm$^3$ of ethyl acetate.

1.1 g of the desired compound are obtained in the form of a precipitate.

Melting point: 95° C.

Crystallisation solvent: ethyl acetate.

EXAMPLE 2

Dihydrochloride of 1-(isoquinolin-5-ylsulphonyl)-4-{N-methyl-N-[4-oxo-4-(p-fluorophenyl)butyl]amino}piperidine

Step A

1-iodo-3-(p-fluorophenylcarbonyl)propane 20 g of 1-chloro-3-(p-fluorophenylcarbonyl)propane dissolved in 100 cm$^3$ of methyl ethyl ketone are refluxed for 24 hours in the presence of 18.5 g of sodium iodide. After treatment, 28 g of the desired compound are isolated.

Step B

1-(isoquinolin-5-ylsulphonyl)-4-{N-methyl-N-[4-oxo-4-(p-fluorophenyl)butyl]amino}piperidine A mixture comprising 4.3 g of the compound obtained in step A, 4.5 g of the compound obtained in step E of Example 1, 2 g of potassium carbonate and 50 cm$^3$ of acetone is refluxed for 12 hours, with stirring. A procedure analogous to that of step G of Example 1 is then followed, yielding 2.1 g of the desired compound.

Step C

Title compound 2.1 g of the compound obtained in the preceding step dissolved in acetonitrile are converted into the dihydrochloride by the addition of 3.4 cm$^3$ of 3N HCl in ether. 2 g of the desired product are obtained.

Melting point: 224°–226° C.

Crystallisation solvent: acetonitrile.

Spectral characteristics

Infra-red: ν (NH+): 2800–1900 cm$^{-1}$;
ν (C=O): 1680 cm$^{-1}$;
ν (N-SO$_2$): 1163 cm$^{-1}$;
NMR: 1H: 9.8 ppm (singlet);
2H+2H: 8.8 to 8.5 ppm (singlet);
2H+1H: 8 ppm (multiplet+triplet);
2H: 7.35 ppm (triplet);
2H: 4 ppm (broad doublet);
2H+3H: 3.5 to 2.9 ppm (2 multiplets);
3H+2H: 2.65 ppm (singlet+triplet);
2H+2H 2.3 to 1.9 ppm (2 multiplets);
2H: 1.8 ppm (multiplet);
2H: 11 ppm exchangeable for D$_2$O.

EXAMPLE 3

Fumarate of 1-(isoquinolin-5-ylsulphonyl)-4-{{N-methyl-N-[3-(p-fluorophenoxy)propyl]amino}methyl}piperidine

Step A

Ethyl 1-(phenylcarbonyl)piperid-4-ylcarboxylate 70 g (0.5 mol) of benzoic acid chloride are poured slowly onto a mixture comprising 78.5 g of ethyl isonipecotate, 50.5 g of triethylamine and 700 cm$^3$ of methylene chloride.

The mixture is left at room temperature for one night and then evaporated. The residue is taken up in ether, washed with water and dried.

There are obtained 106.8 g of an oil which corresponds to the desired compound.

Step B

1-(phenylcarbonyl)piperid-4-ylcarboxylic acid 43.3 g (0.15 mol) of the compound obtained in the preceding step are hydrolysed with 16 cm$^3$ of 1N sodium hydroxide in 160 cm$^3$ of ethanol at room temperature. After treatment, 31.8 g of the desired compound are obtained.

Yield: 91%.

Melting point: 130°–133° C.

Step C

N-methyl-1-(phenylcarbonyl)piperid-4-ylcarboxamide 0.136 mol of the compound obtained in the preceding step is dissolved in 150 cm$^3$ of methylene chloride. 22.1 g of carbonyldiimidazole are added in a single batch. When the evolution of gas has ceased, a freshly prepared solution of 0.5 mol of methylamine in 150 cm$^3$ of methylene chloride is quickly added dropwise.

The mixture is stirred for 12 hours. It is decanted into a separating funnel, dried with water and evaporated.

Yield: 58%.

Melting point: 182°–184° C.

Step D

1 benzyl-4-(methylaminomethyl)piperidine 0.088 mol of the compound obtained in the preceding step in 300 cm$^3$ of tetrahydrofuran is reduced by the addition of a suspension of 6.7 g of lithium aluminium hydride in 100 cm$^3$ of tetrahydrofuran. The mixture is refluxed for 4 hours. After treatment, there are obtained 15.1 g of oil which corresponds to the desired compound. The compound is purified by chromatography over silica using as eluant a methylene chloride/methanol/ammonium hydroxide mixture (89/10/1).

Yield: 52%.

Step E

1-bromo-3-(p-fluorophenoxy)propane

Following the procedure of step F of Example 1, but replacing 1,4-dibromobutane with 1,3-dibromopropane, the desired compound is obtained.

Step F 1-benzyl-4-{{N-methyl-N'-[3-(p-fluorophenoxy)propyl]amino}methylpiperidine A mixture comprising 8.9 g of the compound obtained in step D, 10.3 g of the compound obtained in step E, 6.4 g of potassium carbonate and 170 cm$^3$ of acetone is prepared. The mixture is refluxed for 12 hours. It is concentrated, the residue is taken up in ether and washed with water, and the ethereal phase is exhaustively extracted with 1N hydrochloric acid. The acidic phases are rendered basic, while cold, and extracted with ether. Drying and evaporation yield 13.3 g of an oil which corresponds to the desired compound and which will be used without further purification.

Yield: 78%.

Step G

4-{{N-methyl-N-[3-(p-fluorophenoxy)propyl]amino}methyl}piperidine 0.036 mol of the compound obtained in the preceding step is hydrogenated under 5 kg of pressure/cm$^2$ in 150 cm$^3$ of ethanol and 2.1 g of acetic acid, in the presence of 1.4 g of palladium hydroxide. After treatment, 4.8 g of the desired compound are obtained.

Yield: 42%.

Step H 1-(isoquinolin-5-ylsulphonyl)-4-{{N-methyl-N[3-(p-fluorophenoxy)propyl]amino}methyl}piperidine Following the procedure of step D of Example 1, but using the compound obtained in step G of the present Example, the desired compound is obtained.

Step I

Title compound 3.6 g of the compound obtained in the preceding step are treated with 40.7 cm$^3$ of a 0.172 molar solution of fumaric acid in ethanol.

2 g of the title compound are obtained.
Melting point: 127°–129° C.
Crystallisation solvent: ethanol.

EXAMPLE 4

Fumarate of 1-(isoquinolin-5-ylsulphonyl)-4 {N-methyl N-[5-(p-fluorophenoxy)pentyl]amino}piperidine Following the procedure of Example 1, but replacing 1,4-dibromobutane in step F with 1,5-dibromopentane, the title compound is obtained.
Final yield: 16%.
Melting point: 150° C.
Crystallisation solvent: ethyl acetate.

EXAMPLE 5

Dihydrochloride of 1-(isoquinolin-5-ylsulphonyl)-4-{N-methyl-N-[4-(p-fluorophenyl)-4-oxobutyl]aminomethyl}piperidine

Step A 1-benzyl-4-{N-methyl-N-[4-(p-fluorophenyl)-4-oxobutyl]aminomethyl}piperidine Following the procedure of step F of Example 3, starting from 1-benzyl-4-(methylaminomethyl)piperidine and 1-iodo-3-[(p-fluorophenyl)carbonyl]propane, in the presence of potassium carbonate and in acetone as solvent, the desired compound is obtained in the form of an oil, in a yield of 77%.

Step B

4-{N-methyl-N-[4-(p-fluorophenyl)-4-oxobutyl]aminomethyl}piperidine

Following the procedure of step G of Example 3, the desired compound is obtained in the form of an oil by hydrogenation of the compound obtained in step A above.

Step C 1-(isoquinolin-5-ylsulphonyl)-4-{N-methyl-N-[4-(p-fluorophenyl)-4-oxobutyl]aminomethylpiperidine Following the procedure described in step G of Example 1, starting from the compound obtained in step B above and isoquinolin-5-ylsulphonyl chloride, the desired compound is obtained in the form of an oil.
Yield: 29%.

Step D

Dihydrochloride of 1-(isoquinolin-5-ylsulphonyl)-4-{N-methyl-N-[4-(p-fluorophenyl)-4-oxobutyl]aminoethyl}piperidine Following the procedure of step C of Example 2, the compound obtained in the preceding step is converted into the corresponding dihydrochloride; instantaneous m.p. (K): 148° C.

EXAMPLE 6

In Vitro Pharmacological Study of the Compounds of the Invention

A. Anti-vasoconstrictive activity

Equipment and methods

The studies are carried out on rings, having a length of 3 mm, of aortas removed from WISTAR rats (325–375 g) which have been anaesthetised with sodium pentobarbital (30 mg/kg i.p.); or of aortas removed from New Zealand rabbits (1.8–2 kg) which have likewise been anaesthetised with sodium pentobarbital (30 mg/kg i.p.).

The vascular rings are immersed in a physiological solution, normal or calcium-free (+0.2 mM of EGTA chelator), which is kept at a temperature of 37° C. and aerated with a mixture of 95% $O_2$+5% $CO_2$. The rings are connected to a STATHAM (UC2-GOULD) tension sensor. The optimum tensions for each vessel are applied and a stabilisation period of 90 minutes for the specimens is observed.

a) Anti-vasoconstrictive activity of the compounds of the invention in physiological medium Test protocols The relaxant activity of the compounds of the invention, which were tested in cumulative concentrations added every 15 minutes, with regard to the contraction of vascular rings induced by a hyperpotassic medium (80 mM KCl, 37 mM NaCl) enabled the IC50 (molar concentration that inhibits by 50% the maximum contraction) to be calculated.

Results

Table (T1) summarises the IC50s obtained with the compounds of the Examples representing the compounds of the invention, with regard to the contraction of rat aortas induced by a hyperpotassic medium.

TABLE (T1)

CONCENTRATION INHIBITING BY 50% (IC50) THE CONTRACTION OF RAT AORTAS INDUCED BY POTASSIUM DEPOLARISATION

| Example no tested | 1 | 2 | 3 |
|---|---|---|---|
| IC$_{50}$ (in M) | $9.2 \times 10^{-6}$ | $3.3 \times 10^{-6}$ | $1.5 \times 10^{-6}$ | b) Anti-vasoconstrictive activity of the compounds of the invention in calcium-free medium.

Test protocols

The inhibitory effect of a concentration of the compounds of the invention incubated for 30 minutes, with regard to vascular contraction induced by nonadrenaline ($10^{-6}$ M), is tested.

B. Protective activity on the myocardium a) Effect of the compounds of the invention on the toxic effects of ouabain on the left auricle of guinea-pigs Test protocol The left auricles are removed from guinea-pigs (350–450 g) which have been anaesthetised with sodium pentobarbital (30 mg/kg). The auricles are attached to a STATHAM (UC2-GOULD) tension sensor and the initial tension applied is 0.5 grammes. The auricles are stimulated electrically at 1 Hz by means of platinum electrodes.

Toxic effect is achieved by the addition of ouabain ($10^{-6}$ M). The test compounds are added 15 minutes prior to the addition of the toxic agent.

Results

| | Effect of the products of Examples 2 and 3 on the toxic effects of ouabain on the left auricle of guinea-pigs | | |
|---|---|---|---|
| | SOLVENT H$_2$O (n = 5) | Example 2 $10^{-5}$ M (n = 5) | Example 3 $10^{-5}$ M (n = 4) |
| % CONTRACTION | | | |
| 10 MIN | 207.8 ± 17.4 | 184.0 ± 17.3 | 183.3 ± 20.7 |
| 30 MIN | 80.4 ± 19.4 | 138.8 ± 34.9 | 155.4 ± 15.0 |
| 60 MIN | 19.6 ± 7.7 | 112.2 ± 31.0 | 130.7 ± 34.5 |
| % CONTRACTURE | | | |
| 15 MIN | 2.4 ± 1.2 | 1.4 ± 1.4 | 0.9 ± 0.9 |
| 30 MIN | 40.3 ± 16.3 | 10.5 ± 4.7 | 7.7 ± 1.5 |
| 60 MIN | 93.2 ± 23.9 | 33.5 ± 16.4 | 21.8 ± 6.2 |

| | Effect of the products of Examples 1, 4 and 5 on the toxic effects of ouabain on the left auricle of guinea-pigs | | | | |
|---|---|---|---|---|---|
| | SOLVENT DMSO | Example 1 $10^{-5}$ M | Example 4 $10^{-5}$ M | SOLVENT H$_2$O | Example 5 $10^{-5}$ M |
| % CONTRACTION | | | | | |
| 10 MIN | 202.6 ± 16.5 | 254.7 ± 22 | 213.9 ± 22 | 190.7 ± 14.8 | 206.1 ± 21 |
| 30 MIN | 69.0 ± 13.1 | 260.6 ± 29 | 208.6 ± 22 | 51.3 ± 6.6 | 186.1 ± 21.2 |
| 60 MIN | 24.7 ± 6.1 | 253.6 ± 26 | 211.1 ± 30 | 48.7 ± 15.0 | 141.3 ± 25.3 |
| % CONTRACTURE | | | | | |
| 15 MIN | 0 | 0 | 0 | 7.3 ± 3.4 | 0 |
| 30 MIN | 23.2 ± 8.4 | 0 | 0 | 70.2 ± 14.5 | 2.8 ± 2.1 |
| 60 MIN | 102.8 ± 12.8 | 4 ± 4 | 0 | 87.6 ± 9.8 | 16.5 ± 9.5 |

Results

Table (T2) shows the activity of the compounds of the invention with regard to the contraction of rabbit aortas induced by nonadrenaline in calcium-free medium.

(T2)

% INHIBITION OF THE CONTRACTION INDUCED BY NORADRENALINE IN CALCIUM-FREE MEDIUM

| | Concentration of compound | |
|---|---|---|
| Example no. tested | $10^{-6}$ M | $10^{-7}$ M |
| 1 | 62 | |
| 2 | 86 | 50 |
| 3 | 82 | 43 |

Conclusion

The compounds of the invention have a remarkable inhibitory activity with regard to the vascular contraction induced by potassium depolarisation. It is very interesting that those products are also active with regard to contraction induced by a vasoconstrictive mediator, such as nonadrenaline, even in the absence of extracellular calcium.

These results show that the compounds of the present invention oppose considerably the development of contracture (expressed as a percentage of the initial contraction developed) and the collapse of the developed contraction, which are associated with the toxic effects of ouabain.

b) Protective effect of the compounds of the invention on an isolated heart subjected to hypoxia-reoxygenation Test protocol The heart is removed from WISTAR rats (325-375 g). The heart is perfused rapidly according to the technique of LANGENDORFF at a constant pressure of 76 mmHg and is stimulated electrically at 5 Hz.

The heart is subjected to hypoxia for 60 minutes, which is effected by the administration of a gaseous mixture of 95% N$_2$ + 5% CO$_2$ during that period, and is followed by reoxygenation for 30 minutes.

The test compounds are incubated for 15 minutes prior to and for the duration of the hypoxia.

The isovolumetric contractions are recorded by means of a polyethylene balloon connected to a pressure sensor (P23-GOULD) introduced into the left ventricle and inflated so as to obtain a diastolic pressure of between 5 and 10 mm of mercury.

Results

Protective effect of the products of Example 2 and 3 on an isolated rat's heart subjected to hypoxia-reoxygenation

| | SOLVENT H$_2$O (n = 7) | Example 2 8·10$^{-7}$ M (n = 4) | Example 3 8·10$^{-7}$ M (n = 5) |
|---|---|---|---|
| % PVG at 30 min DE REOXYGENATION | 45.2 ± 10 | 95.0 ± 1.9 | 85.4 ± 5.8 |
| CONTRACTURE AMPLITUDE (mmHg) | | | |
| at 10 min hypoxia | 21.1 ± 3.2 | 12.5 ± 2.2 | 20.8 ± 4.6 |
| at 30 min hypoxia | 35.1 ± 6.6 | 12.5 ± 3.0 | 26.0 ± 5.1 |
| at 60 min hypoxia | 31.4 ± 6.8 | 11.5 ± 2.6 | 25.6 ± 2.9 |
| at 15 min reoxygenation | 20.9 ± 5.9 | 5.5 ± 4.3 | 9.6 ± 2.4 |
| at 30 min reoxygnation | 12.3 ± 4.3 | 0.5 ± 0.5 | 1.6 ± 1.0 |

These results show that the compounds of the present invention also limit the development of contracture during hyposia and permit improved functional recovery during reoxygenation.

Conclusion

Test studies therefore show that the compounds of the present invention protect the myocardium effectively with regard to an overload of intracellular calcium (ouabain intoxication) or with regard to hypoxia-reoxygenation.

We claim:

1. A compound selected from those of formula (I):

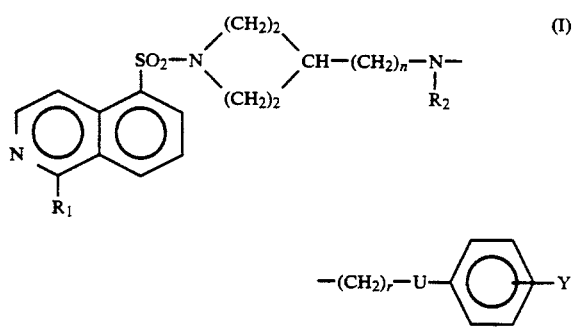

in which:
n is 0 or 1 to 3 inclusive,
r is 1 to 6 inclusive,
R$_1$ represents hydrogen, hydroxy, or chlorine,
R$_2$ represents:
  hydrogen
  formyl,
  —A, —CO—A or —CO—O—A, wherein A represents lower alkyl, lower alkenyl, lower alkynyl, cycloalkyl, or cycloalkyl-lower alkyl,
  —(CH$_2$)$_q$-phenyl or substituted —(CH$_2$)$_q$-phenyl, wherein q represents 0 to 1 to 4 inclusive,
  —CO-phenyl or substituted —CO-phenyl,
  —CO—O-phenyl or substituted —CO—O-phenyl, or
  —CO—NR$_4$R$_5$ wherein R$_4$ and R$_5$ which may be identical or different, each represent hydrogen or a group selected from lower alyl, lower alkenyl, lower alkynyl, phenyl and phenyl-lower alkyl, or
  together with the nitrogen atom carrying them, form a saturated ring having 4 to 7 ring members, inclusive,
Y is para-fluoro,
U represents oxygen or carbonyl,
wherein:
  the term "substituted " relating to the groups —(CH$_2$)$_q$—phenyl, —CO-phenyl, or —CO—O-phenyl means that those groups may be substituted by one or more radicals selected from: lower alkyl, lower alkoxy, hydroxy, halogen, and trifluoromethyl,
  the terms "lower alkyl" and "lower alkoxy" indicate straight-chain or branched saturated carbon-containing groups having 1 to 6 carbon atoms, inclusive,
  the terms "lower alkenyl" and "lower alkynyl" designate straight-chain or branched unsaturated groups having 2 to 6 carbon atoms, inclusive, and
  the term "cycloalkyl" designates a saturated carbon-containing ring having 3 to 8 ring members, inclusive, optical isomers thereof and, where applicable, the addition salts thereof with a pharmaceutically-acceptable acid.

2. A compound according to claim 1 which is 1-(isoquinolin-5-ylsulphonyl)-4-{N-methyl-N-[4-(p-fluoro-phenoxy) butyl]amino]piperidine, as well as the addition salts thereof with a pharmaceutically-acceptable acid.

3. A compound according to claim 1 which is 1-(isoquinolin-5-ylsulphonyl)-4-{N-methyl-N-[4-oxo-4-(p-fluorophenyl) butyl]amino}piperidine, as well as the addition salts thereof with a pharmaceutically-acceptable acid.

4. A compound according to claim 1 which is 1-(isoquinolin-5-ylsulphonyl)-4-{{N-methyl-N-[3-(p-fluorophenoxy) propyl]amino}methyl}piperidine, as well as the addition salts thereof with a pharmaceutically-acceptable acid.

5. A compound according to claim 1 which is 1-(isoquinolin-5-ylsulphonyl)-4-(N-methyl-N-[5-(p-fluorophenoxy) pentyl]amino}piperidine, as well as the addition salts thereof with a pharmaceutically-acceptable acid.

6. A compound according to claim 1 which is 1-(isoquinolin-5-ylsulphonyl)-4-{N-methyl-N-[4-(p-fluorophenyl) -4-oxobutyl] aminomethyl}piperidine, as well as the addition salts thereof with a pharmaceutically-acceptable acid.

7. A pharmaceutical composition useful in combating tissue damage containing as active ingredient an effective amount of a compound of claim 1 in combination with one or more pharmaceutically-acceptable excipients or vehicles.

8. A method for treating a living animal body afflicted with a disorder due to or associated with tissue damage, comprising the step of administering to the said body an amount of a compound of claim 1 which is effective for alleviation of the said disorder.

* * * * *

UNITED STATES PATENT AND TRADEMARK OFFICE
CERTIFICATE OF CORRECTION

PATENT NO. : 5,298,503

DATED : March 29, 1994   Page 1 of 2

INVENTOR(S) : Jean-Louis Peglion, Jean-Paul Vilaine, Nicole Villeneuve, and Philip Janiak It is certified that error appears in the above-indentified patent and that said Letters Patent is hereby corrected as shown below:

Title page, col. 2,
ABSTRACT [57]; the formula should NOT be hyphenated, but the two (2) dashes should be connected and should read as just one (1) hyphen in the middle of the formula.

Col. 1, approximately lines 13-23; the formula should NOT be hyphenated, but the two (2) dashes should be connected and should read as just one (1) hyphen in the middle of the formula.

Col. 6, line 3; insert a hyphen after "1".

Col. 6, line 37; insert a hyphen between "1" and "bromo".

Col. 6, line 40; "0 5 mol" should read -- 0.5 mol --.

Col. 8, line 49; insert a hyphen between "1" and "benzyl".

Col. 9, line 5; insert a -- } -- between "methyl" and "piperidine".

Col. 9, line 30; insert a hyphen at the end of the line, after "N".

Col. 9, line 47; insert a hyphen at the end of the line, after "methyl".

Col. 10, line 15; "oxobutyl}aminomethylpiperidine" should read -- oxobutyl]aminomethyl}piperidine --.

Col. 13, line 9; "REOXYGENATION" should be underlined so as to separate it from the next line which reads "CONTRACTURE".

Col. 13, line 17; "reoxygnation" should read -- reoxygenation --

Col. 13, line 21; "hyposia" should read -- hypoxia --.

Col. 13, approximately lines 35-44; the formula should NOT be hyphenated, but the two (2) dashes should be connected and should read as just one (1) hyphen in the middle of the formula.

UNITED STATES PATENT AND TRADEMARK OFFICE
CERTIFICATE OF CORRECTION

PATENT NO. : 5,298,503

DATED : March 29, 1994

INVENTOR(S) : Jean-Louis Peglion, Jean-Paul Vilaine, Nicole Villeneuve, and Philip Janiak It is certified that error appears in the above-indentified patent and that said Letters Patent is hereby corrected as shown below:

Col. 14, line 3; "alyl" should read -- alkyl --.
Col. 14, line 25; insert the words -- the possible -- before "optical".
Col. 14, line 30; "amino]piperidine" should read -- amino}piperidine --.
Col. 14, line 44; "4-(N" should read -- 4-{N --.

Signed and Sealed this

Twentieth Day of September, 1994

Attest:

BRUCE LEHMAN

Attesting Officer

Commissioner of Patents and Trademarks